(12) United States Patent
Nagaoka et al.

(10) Patent No.: US 8,785,698 B2
(45) Date of Patent: Jul. 22, 2014

(54) METHODS AND APPARATUS FOR PRODUCTION OF NATURAL L-MENTHOL

(75) Inventors: Ryosuke Nagaoka, Kobe (JP); Hideaki Izukura, Kobe (JP); Susumu Tokita, Nishinomiya (JP); Yuri Shibata, Kobe (JP); Yoshiyuki Nagaoka, Kobe (JP)

(73) Assignee: Nagaoka & Co., Ltd., Nishinomiya-shi (JP)

( * ) Notice: Subject to any disclaimer, the term of this patent is extended or adjusted under 35 U.S.C. 154(b) by 0 days.

(21) Appl. No.: 13/148,929

(22) PCT Filed: Feb. 17, 2010

(86) PCT No.: PCT/IB2010/000434
§ 371 (c)(1),
(2), (4) Date: Aug. 10, 2011

(87) PCT Pub. No.: WO2010/095034
PCT Pub. Date: Aug. 26, 2010

(65) Prior Publication Data
US 2011/0313205 A1    Dec. 22, 2011

Related U.S. Application Data

(60) Provisional application No. 61/153,258, filed on Feb. 17, 2009.

(51) Int. Cl.
| | | |
|---|---|---|
| C07C 35/12 | (2006.01) |
| A23L 1/226 | (2006.01) |
| B01D 9/00 | (2006.01) |
| C07C 29/78 | (2006.01) |
| C11B 9/02 | (2006.01) |

(52) U.S. Cl.
CPC ............. *B01D 9/0013* (2013.01); *A23L 1/2265* (2013.01); *C07C 29/78* (2013.01); *C07B 2200/07* (2013.01); *C11B 9/022* (2013.01); *C07C 2101/14* (2013.01)
USPC ........................................................ 568/829

(58) Field of Classification Search
None
See application file for complete search history.

(56) References Cited

U.S. PATENT DOCUMENTS

| | | | |
|---|---|---|---|
| 2,139,390 | A | 12/1938 | Terwilliger et al. |
| 2,662,052 | A | 12/1953 | Bridger et al. |

(Continued)

FOREIGN PATENT DOCUMENTS

| | | |
|---|---|---|
| DE | 10 2005 040655 | 3/2007 |
| GB | 397212 | 8/1933 |

(Continued)

OTHER PUBLICATIONS

"Crystallization" in Kirk-Othmer Encyclopedia of Chemical Technology, Joachim Ulrich; Published Online: Aug. 16, 2002, Copyright © 2001 by John Wiley & Sons, Inc., pp. 95-147.*

(Continued)

*Primary Examiner* — Karl J Puttlitz
(74) *Attorney, Agent, or Firm* — Knobbe Martens Olson & Bear LLP

(57) ABSTRACT

Embodiments are provided that provide for efficient production of highly pure natural l-menthol. In some embodiments, a method for preparing natural l-menthol involves providing crude mentha oil in a crystallizer and gradually reducing the temperature of the crystallizer in a step-wise manner, thereby producing highly pure crystals in less than two weeks. The methods disclosed herein are suitable for pharmaceutical GMP.

8 Claims, 7 Drawing Sheets

(56) References Cited

U.S. PATENT DOCUMENTS

Figure 1:
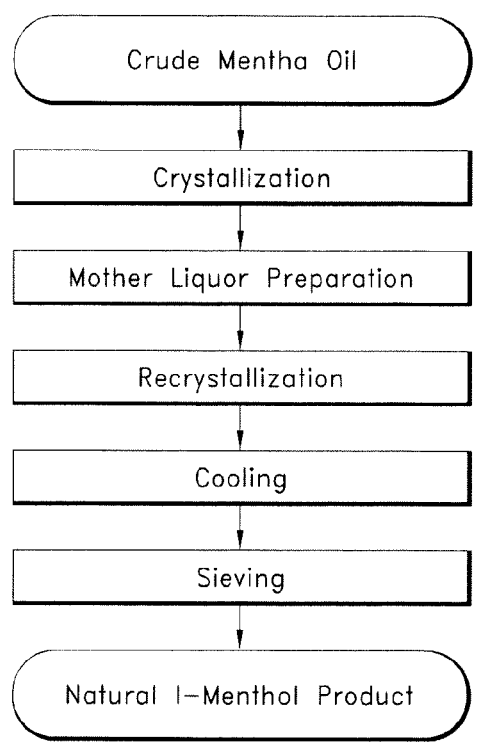

| | | | |
|---|---|---|---|
| 3,023,253 A * | 2/1962 | Bain et al. .................... 568/829 |
| 3,607,651 A | 9/1971 | Moroe et al. |
| 3,943,181 A | 3/1976 | Fleischer et al. |
| 4,011,270 A | 3/1977 | Carrington |
| 4,418,225 A | 11/1983 | House |
| 4,487,956 A | 12/1984 | Suzukamo et al. |
| 5,019,658 A | 5/1991 | Cahn |
| 5,773,410 A | 6/1998 | Yamamoto |
| 6,342,644 B1 | 1/2002 | Sayo et al. |
| 6,706,500 B2 | 3/2004 | Gatfield et al. |
| 7,268,228 B2 | 9/2007 | Lee et al. |
| 7,459,587 B2 | 12/2008 | Nakayasu et al. |
| 7,468,463 B2 | 12/2008 | Johann et al. |
| 7,709,688 B2 | 5/2010 | Bergner et al. |
| 2002/0019573 A1 | 2/2002 | Schlemenat et al. |
| 2003/0153031 A1 | 8/2003 | Chaplin et al. |
| 2004/0058422 A1 | 3/2004 | Chaplin et al. |
| 2005/0169987 A1 | 8/2005 | Korber |
| 2008/0139852 A1 | 6/2008 | Bergner et al. |
| 2008/0214877 A1 | 9/2008 | Rauls et al. |
| 2008/0228013 A1 | 9/2008 | Nakayasu et al. |
| 2009/0011238 A1 | 1/2009 | Rheinlander et al. |
| 2010/0185024 A1 * | 7/2010 | Rauls et al. .................... 568/840 |
| 2010/0206712 A1 | 8/2010 | Heydrich et al. |

FOREIGN PATENT DOCUMENTS

| | | |
|---|---|---|
| GB | 376356 | 4/1934 |
| IN | 134735 | 9/1973 |
| IN | 147337 | 2/1980 |
| IN | 150447 | 10/1982 |
| IN | 150459 | 10/1982 |
| IN | 151863 | 8/1983 |
| IN | 179087 | 8/1997 |
| IN | 182739 | 7/1999 |
| JP | S46-026933 | 8/1971 |
| JP | S57-200321 | 12/1982 |
| JP | H09-217084 | 8/1997 |
| JP | 2008-230978 | 10/2008 |
| SU | 1092341 * | 5/1984 |
| WO | WO/03/101924 | 12/2003 |
| WO | WO 2006/097427 | 9/2006 |
| WO | WO 2009/033870 | 3/2009 |

OTHER PUBLICATIONS

Tandon et al., Journal of Medicinal and Aromatic Plant Sciences, vol. 20, No. 1, 1998, pp. 25-27.*

Tandon, S.; Aggarwal, K. K., Kahol, A. P.; Ahmad, J.; Kumar, Sushil; "Yield and quality of the menthol crystals and dementholated oil recovered from the essential oils of the *Mentha arvensis* cultivars Shivalik and Himalaya" Journal of Medicinal and Aromatic Plant Sciences, vol. 20, No. 1, 1998, pp. 25-27, XP009135909 p. 25, col. 2, line 6-line 20.

International Search Report issued on Jul. 27, 2010 for PCT Publication No. WO/2010/095034.

Haut, et al., "Synthesis and Purification of Menthol Isomers", Tobacco Documents Online, Philip Morris U.S.A. Research Center Completion Report, Jan. 10, 1981. Web. Oct 3, 2008.

Sulzer Chemtech Ltd., Brochure entitled "Fractional Crystallization."

Japanese Office Action dated Apr. 22, 2014 for Japanese Application No. 2011-549696.

* cited by examiner

METHODS AND APPARATUS FOR PRODUCTION OF NATURAL L-MENTHOL

CROSS-REFERENCING TO RELATED APPLICATIONS

The present application claims the benefit of priority to U.S. Provisional Application No. 61/153,258, filed Feb. 17, 2009. The priority document is hereby incorporated by reference in its entirety.

FIELD

The present disclosure relates to a method and apparatus for the production of l-menthol.

INTRODUCTION

Menthol, particularly l-menthol, is an important substance widely used in the field of, for example, food additives, drug components, cosmetics, fragrances and medicines. l-Menthol is the main component of the mentha oils from *Mentha arvensis* and *Mentha piperita*. l-Menthol is generally obtained from the crude mentha oil by crystallization. Depending on the crystallization method and the starting material, the crystals differ in terms of taste, size and shape. Residual liquid mentha oil adhering to the menthol crystals obtained from mentha oils affects the sensory profile of the crystals. l-Menthol has conventionally been used as a flavor for food, including sweets and oral refreshments such as, for example, chewing gum, candy, cigarettes and the like. The presence of trace amounts of impurities can detrimentally affect the quality and flavor of l-menthol, and therefore, processes for producing highly pure l-menthol have been of interest for a long time.

l-Menthol is commercially available in solid forms such as powders, crystals, solidified distillate, flakes and pressed articles. In general, natural l-menthol is purified from crude mentha oil, such as by recrystallization of oil from *Mentha arvensis*. Such l-menthol production methods, however, involve production times of greater than two weeks to a month. In these previous l-menthol production methods, native crude mentha oil cannot be used directly for the crystallization process. Rather, the methods require an initial crystallization to prepare crude l-menthol from the crude mentha oil, and then a recrystallization step to prepare purified l-menthol product. In addition, previously known methods for producing l-menthol have involved significant manual labor and handling of the process materials. Because of the necessity of handling the mentha oil and the resulting l-menthol crystals, adaptation of these l-menthol production processes to Good Manufacturing Practice (GMP) regulation is likely to be difficult.

SUMMARY

The present teachings provide, among other things, methods and apparatus for production of highly pure natural l-menthol.

Various embodiments of a method of the present teachings comprise crystallizing l-menthol from crude mentha oil by gradual cooling in a container; and purifying the resulting crystals in the same container.

Some embodiments disclosed herein include a method for purifying l-menthol, comprising providing crude mentha oil in a crystallizer; crystallizing l-menthol from the crude mentha oil by gradually reducing temperature in the crystallizer; passing a fluid over the l-menthol crystals to remove residual oil and impurities, wherein purified l-menthol crystals of at least 98% purity by weight are obtained; melting the purified l-menthol crystals to remove l-menthol from the crystallizer as a melt; and cooling the melt into a dried, solid l-menthol product, wherein the method is performed in a closed system without human contact with the crude mentha oil or the l-menthol.

In some embodiments, the crude mentha oil is of plant origin.

In some embodiments, the l-menthol product has a purity of at least 99% by weight. In some embodiments, the l-menthol product has a purity of at least 99.4% by weight.

In some embodiments, the crude mentha oil comprises l-menthol in the range of about 30% to about 95% by weight. In some embodiments, the l-menthol concentration in the crude mentha oil is in the range of about 50% to about 90% by weight. In some embodiments, the crude mentha oil contains less than about 30% by weight of an organic solvent. In some embodiments, the crude mentha oil is substantially free of added organic solvent.

In some embodiments, the temperature in the crystallizer is gradually reduced to 41° C. In some embodiments, the temperature in the crystallizer is gradually reduced to between about −30° C. to about 30° C.

In some embodiments, the method further comprises comminuting the solid l-menthol product into particulate. In some embodiments, the particulate are pellets.

In some embodiments, the method further comprises extruding the solid l-menthol product, wherein said comminuting the solid l-menthol product is cutting the extruded solid l-menthol product. In some embodiments, the pellets are formed using a pelletizer fluidly coupled to the crystallizer.

In some embodiments, the method further comprises introducing seed crystals of l-menthol into the crystallizer to aid crystallizing l-menthol. In some embodiments, introducing seed crystals of l-menthol comprises adding pre-formed seed crystals of l-menthol.

In some embodiments, said introducing seed crystals of l-menthol comprises rapidly cooling a portion of the crude mentha oil to form the l-menthol seed crystals. In some embodiments, said rapidly cooling a portion of crude mentha oil comprises exposing the portion of crude mentha oil to a surface having a temperature of no more than about 10° C. In some embodiments, the surface has a temperature in the range of about 0° C. to about 20° C.

In some embodiments, the method further comprises removing residual oils and impurities while gradually elevating the temperature in the crystallizer.

In some embodiments, the method further comprises applying reduced or increased pressure to aid removing residual oils and impurities while gradually elevating the temperature in the crystallizer. In some embodiments, the l-menthol crystals are gradually elevated to a temperature in the range of about 35° C. to about 40° C. In some embodiments, the fluid is a gas. In some embodiments, the gas is selected from the group consisting of air, N2, an inert gas and combinations thereof.

In some embodiments, the purified l-menthol crystals are obtained by crystallizing the crude mentha oil only once.

Some embodiments disclosed herein include a system for purifying l-menthol, comprising a crystallizer containing crude mentha oil of plant origin; a stripping system adapted to pass a gas through the crystallizer; an automated process control system comprising a processor programmed to: initiate reduction of a temperature in the crystallizer in order to reduce the temperature of the crude mentha oil from a temperature at which the crude mentha oil is a liquid to a temperature below 30° C. in a gradual manner over a period of at least 8 hours to cause I-menthol crystals to form in the crystallizer; activate the stripping system in order to pass the gas over the crystals in the crystallizer to remove liquid from the crystals; and initiate heating of the crystallizer in order to melt the crystals, and a conduit configured to receive melted I-menthol from the crystallizer, wherein the crystallizer and the conduit together comprise a closed system that prevents contact between the content of the closed system and outside contaminants.

In some embodiments, the crude mentha oil comprises I-menthol in the range of about 30% to about 95% by weight. In some embodiments, the I-menthol concentration in the crude mentha oil is in the range of about 30% to about 50% by weight.

In some embodiments, the crystallizer comprises a plurality of cooling plates and/or cooling coils. In some embodiments, the automated process control system independently controls the temperature for each of said plurality of cooling plates and/or cooling coils.

In some embodiments, the stripping system is configured to introduce gas under pressure near the top of the crystallizer. In some embodiments, the stripping system is configured to withdraw gas near the bottom of the crystallizer.

In some embodiments, the system further comprises a user control interface in communication with the automated process control system to operate the system.

In some embodiments, the system is automated.

In some embodiments, the system further comprises a crystal formation detector. In some embodiments, said crystal formation detector comprises a light source and light detector configured to detect changes in the optical properties of material in the crystallizer. In some embodiments, said crystal formation detector comprises a heat absorption detection system configured to measure the heat uptake of a cooling surface, and a thermocouple configured to measure the temperature near the cooling surface.

In some embodiments, the automated process control system is configured to receive an identifier corresponding to a measured or estimated I-menthol concentration in the crude mentha oil, wherein the automated process control system selects crystallization conditions in the crystallizer based, at least in part, on the identifier.

In some embodiments, the conduit is in fluid communication with a storage tank, wherein the storage tank is part of the closed system. In some embodiments, the conduit is in fluid communication with a pelletizer, wherein the pelletizer is part of the closed system.

DRAWINGS

FIG. 1 is a flow chart diagram showing an existing method for purifying I-menthol from crude mentha oil.

Figure 2A:
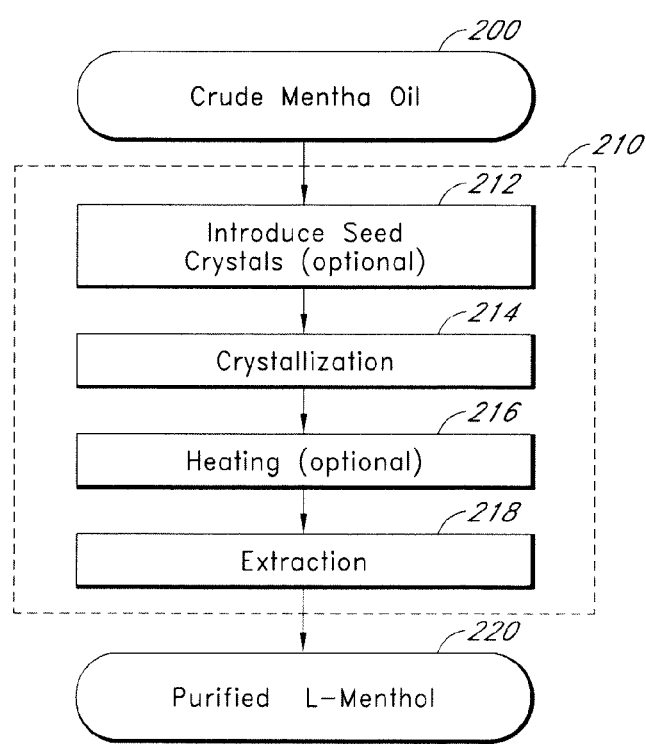
Figure 2B:
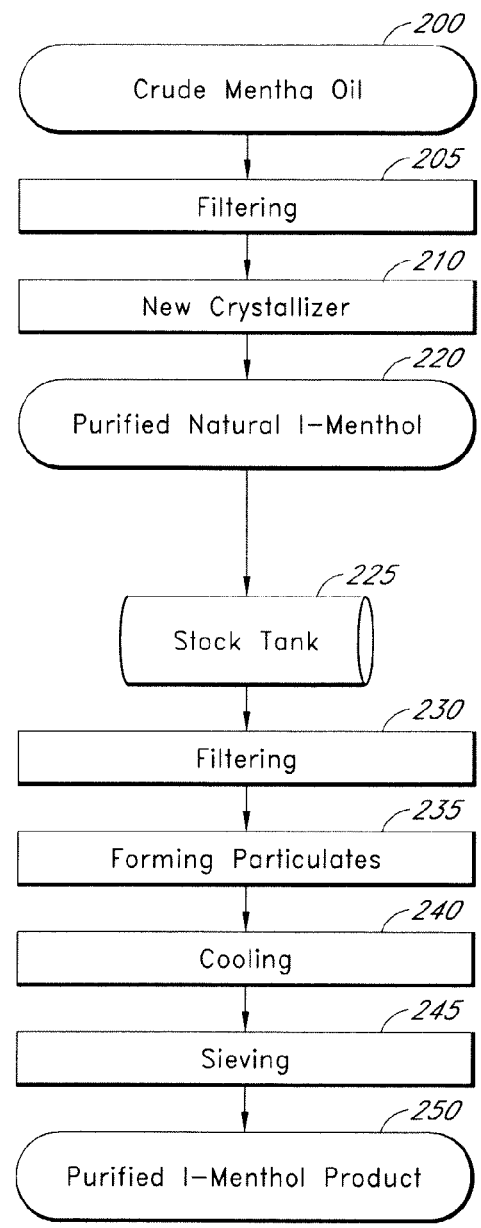

FIG. 2A-B are flow charts illustrating embodiments of methods for producing I-menthol.

Figure 3:
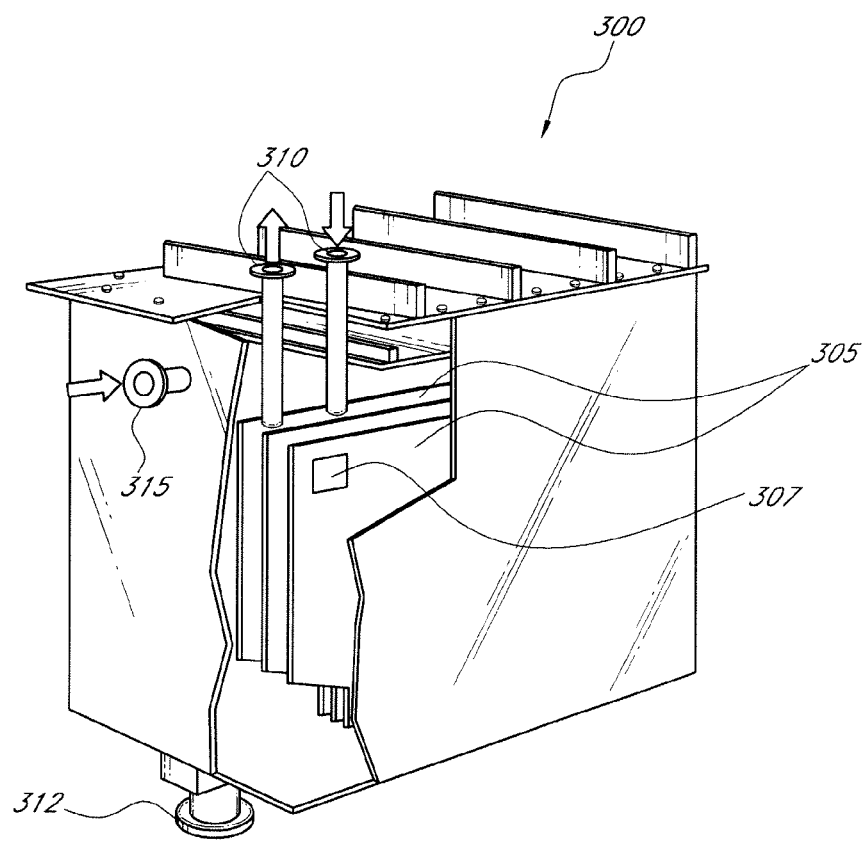

FIG. 3 depicts a cross-sectional of an exemplary crystallizer in some embodiments of the system for purifying I-menthol disclosed herein.

Figure 4A:
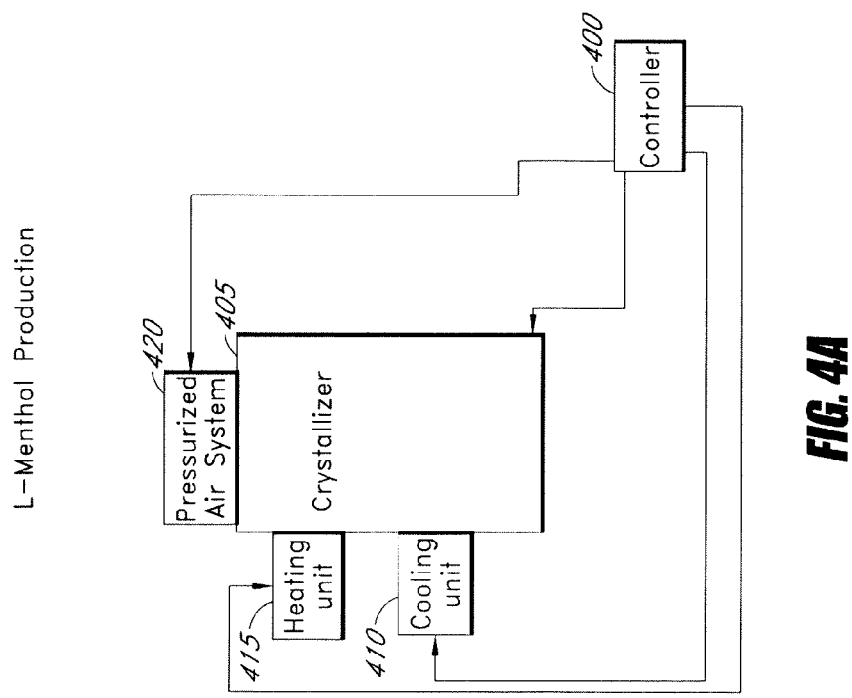
Figure 4B:
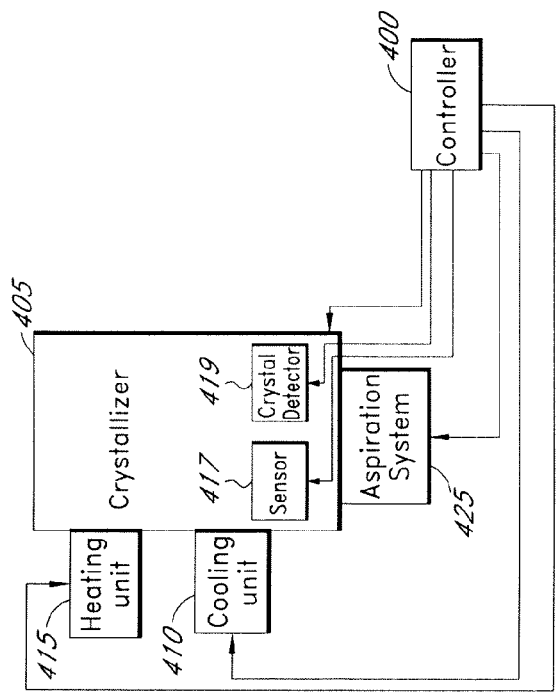
Figure 4C:
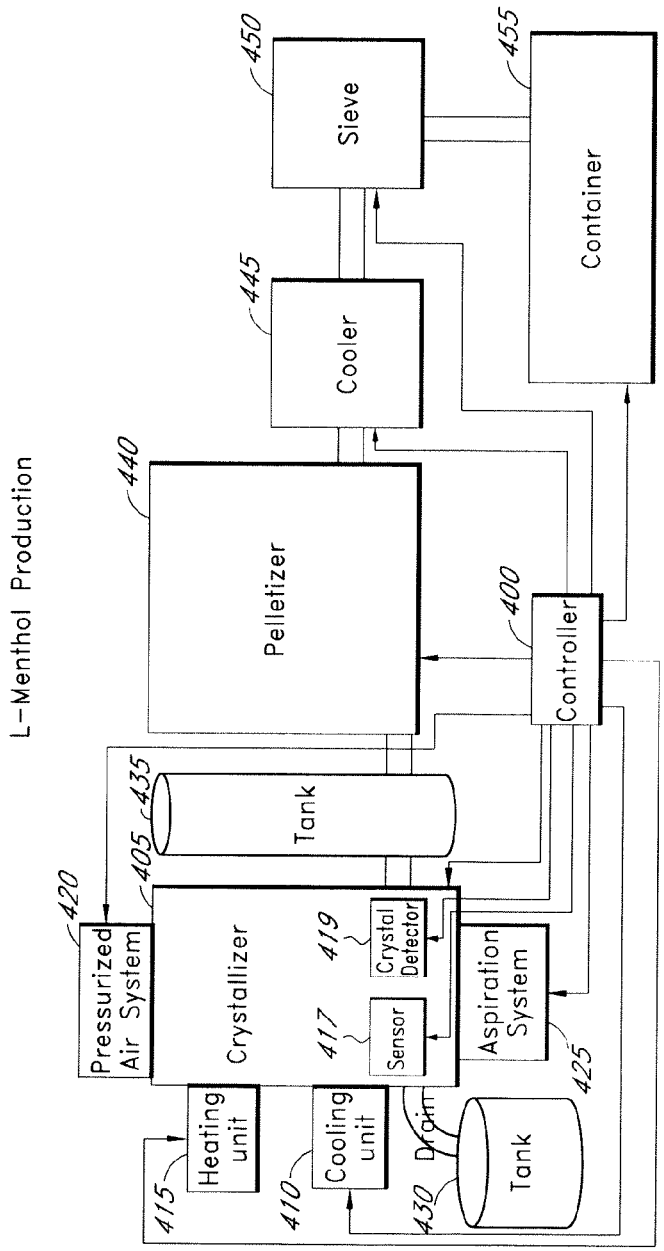

FIG. 4A-C illustrate embodiments of a system for purifying I-menthol.

DESCRIPTION OF VARIOUS EMBODIMENTS

Various embodiments disclosed herein are generally directed towards systems and methods for producing highly pure natural I-menthol.

At present, there are a limited number of techniques that exist for I-menthol production. A diagram of one existing I-menthol production method is shown in FIG. 1. Briefly, crude mentha oil is first crystallized and then dementholized oils are drained away from the crystals. The crude I-menthol crystals are then melted to form a mother liquor, which is adjusted to a desired I-menthol concentration. The mother liquor is subjected to a recrystallization step, after which remaining dementholized oils are drained away. The remaining crystalline I-menthol is then purified and sieved to obtain an I-menthol product.

Until now, the various I-menthol production techniques have been limited because they involve long production times and significant handling of the process materials at various stages. In particular, existing methods for purifying I-menthol from crude mentha oil may require two cycles of crystallization to isolate I-menthol from the crude mentha oil compositions. Furthermore, adaptation of previous I-menthol production processes to GMP regulation is likely to be difficult because of the handling of process materials that is required. Another problem with previous techniques for production of I-menthol is clumping and block formation ("blocking") of the solid product, which can impair pourability and handling of the I-menthol.

A new approach to production of I-menthol has been developed that allows direct preparation of high purity I-menthol from crude mentha oil. In the production process, I-menthol crystals are formed directly from crude oil under controlled cooling of the crude mentha oil in a closed system without the necessity of human contact with the crude mentha oil or I-menthol. Thus, the methods disclosed herein can be easily adapted to GMP regulations, and may be used to produce pharmaceutical grade I-menthol.

In one embodiment, menthol crystals can be further purified in the same enclosed container and no recrystallization or additive to the crude oil is required to obtain highly pure I-menthol, and the method takes significantly less time than previous I-menthol production methods. After purification, the menthol can be formed into pellets of suitable hardness and shape to prevent clumping and block formation of the solid menthol product even in the absence of additives such as silicon dioxide. In some embodiments, the I-menthol production method is entirely hands-free and can readily be adapted to meet pharmaceutical Good Manufacturing Practices (GMP).

Some of the present embodiments involve systems useful for production of I-menthol. For example, the systems can facilitate hands-free, automated (either partially or fully) production of highly pure I-menthol. In some embodiments, a system for production of I-menthol can include a pelletizer to form I-menthol pellets for ease of handling. In some embodiments, a system for production of I-menthol can include a cooler and/or a sieve. In some embodiments, the systems can be adapted for pharmaceutical GMP.

In some embodiments, an apparatus for production of highly pure (greater than about 99.5%) I-menthol is provided. The apparatus may automate, regulate, and maintain temperature during crystallization of I-menthol. In one embodiment, I-menthol production can be carried out using a crystallizer that has been modified to include standard or optional attachments. In other embodiments, I-menthol production can be carried out using a dedicated crystallizer that has been adapted for highly controlled temperature regulation. In other embodiments, a system for fractional crystallization can be adapted for I-menthol production. For example, a fractional crystallizer (e.g., without limitation, the Sulzer™ Static Crystallizer S-1) can be adapted for use in combination with temperature sensors, an aspiration system, a pressurized air system, and/or other components that aid in controlling operation of the crystallizer.

Some of the present embodiments involve methods for producing highly pure l-menthol by crystallization using gradual cooling under controlled temperature conditions. Using such a method, crystallization and purification of l-menthol may be completed in less than about two weeks, compared with nearly a month for previous l-menthol production methods. Thus, certain l-menthol production methods discussed herein may reduce the time for producing pure l-menthol crystals from about two to three weeks to about 12 or fewer days. Depending on the embodiment, production of highly pure l-menthol using the systems and methods described herein may take about 12, 11, 10, 9, 8, 7, 6, 5 or fewer days. Thus, the methods can facilitate faster production of highly pure l-menthol. Furthermore, the decreased time requirements may increase overall production of a particular crystallization system.

As will be appreciated by one of skill in the art, the ability to quickly prepare highly pure l-menthol without handwork can have great benefit, especially for applications where pharmaceutical GMP is desirable. The systems, apparatus and methods described herein allow production of highly pure l-menthol in a shortened period of time (i.e., less than about two weeks) without the need for re-crystallization or handwork.

DEFINITIONS

Unless defined otherwise, all technical and scientific terms used herein have the same meaning as is commonly understood by one of ordinary skill in the art. In the event that there is a plurality of definitions for a term herein, those in this section prevail unless stated otherwise.

As used herein, "crude mentha oil" refers to oils distilled from a mint plant (*Mentha* species), which oils contain at least 30% l-menthol by weight, such as peppermint oil, crude peppermint oil, mint oil and mixtures thereof. "Crude mentha oil" include both "adjusted crude mentha oil" and "native crude mentha oil."

As used herein, "dementholized oil" refers to components of crude mentha oil remaining after at least partially removing l-menthol from the oil.

As used herein, "mother liquor" is menthol-containing oil prepared for the crystallization of l-menthol, as well as the oily liquid remaining after crystallizing crude l-menthol.

As used herein, "native crude mentha oil" refers to mentha oil prepared by steam distillation from mentha plant material. Native crude mentha oil does not include a diluent, such as a solvent.

As used herein, "adjusted crude oil" refers to native crude mentha oil to which l-menthol and/or a diluent (e.g., dementholized oil) has been added, such as to adjust the l-menthol concentration.

As used herein, "automated" refers to performing, or being capable of performing, a method or a part of a method without manually handling or manually moving menthol-containing materials, other than controlling operation of an apparatus or system. As a non-limiting example, a process is automated when a user only presses buttons, operates knobs, or opens or closes valves to initiate various steps of a process performed using one or more apparatuses. Automation may be controlled by one or more controllers (possibly in response to human interaction with the controllers), such as a computing device, analog circuitry, and/or digital circuitry. Automation may also include various sensors that provide feedback to a controller and/or to a human operator that may be used to automatically adjust operation of a crystallization system.

Methods

The l-menthol production methods disclosed herein can be used for direct production of highly pure l-menthol from crude mentha oil. For example, methods disclosed herein can be used to produce l-menthol meeting pharmaceutical GMP. Production of l-menthol according to various methods disclosed herein may take two weeks or less. In some embodiments, the methods are performed in a closed system without human contact with the crude mentha oil or the l-menthol.

With reference now to FIG. 2A, an exemplary method for l-menthol production is illustrated. Depending on the embodiment, the method of FIG. 2A may include fewer or additional blocks and/to the blocks may be performed in a different order than is illustrated.

Crude mentha oil is provided at block 200. The source and type of the crude mentha oil is not particularly limited, and can be obtained, for example, from commercial sources. The crude mentha oil can preferably be of plant origin. In some embodiments, the crude mentha oil is native crude mentha oil prepared by steam distillation from mentha plant material. In some embodiments, the crude mentha oil is adjusted crude mentha oil, where the concentration of l-menthol has been adjusted by dilution, distillation, or the addition of l-menthol.

The concentration of l-menthol in the crude mentha oil is also not particularly limited. The crude mentha oil can, for example, include about 30% to about 95% l-menthol by weight (preferably about 50% to about 90% l-menthol by weight). In some embodiments, the method includes adjusting the concentration of l-menthol in the crude mentha oil to be within a predetermined concentration range of l-menthol. As an example, a person of ordinary skill, guided by the teachings of the present application, could identify optimal concentration ranges that improve various aspects of the present method (e.g., reduced crystallization time, greater l-menthol purity, and the like), and adjust the l-menthol concentration to within an optimal concentration range. Alternatively, the method can be practiced using native crude mentha oil, without any adjustment of concentration.

The crude menthol oil, in some embodiments, includes few, if any, added organic solvents. By avoiding the use of significant amounts of organic solvent, the methods disclosed herein may not require additional steps to remove organic solvents. Furthermore, the methods disclosed herein may be more economical compared to other methods requiring costly organic solvents. In some embodiments, the crude mentha oil contains less than about 30% by weight of an organic solvent. In some embodiments, the crude mentha oil is substantially free of an organic solvent (e.g., no more than trace amounts).

Block 210 represents purifying steps for crude mentha oil performed within a crystallizer. Before crystallizing the l-menthol at block 214, seed crystals of l-menthol may optionally be introduced at block 212 to aid crystallization. Without being bound to any particular theory, it is believed that nucleation limits the crystallization kinetics of l-menthol, and therefore adding seed crystals of l-menthol may improve the rate of crystallization. In some embodiments, pre-formed seed crystals of l-menthol are added to the crude mentha oil in the crystallizer.

Seed crystals of l-menthol may also be introduced, in some embodiments, by rapidly cooling a portion of the crude mentha oil in the crystallizer to form seed crystals of l-menthol. In some embodiments, seed crystals are formed by exposing a portion of the crude mentha oil to one or more cooling surfaces having a temperature of no more than about 20° C. (preferably no more than about 10° C., and more preferably in the range of about 0° C. to about 10° C.). For example, one or more cooling surfaces within the crystallizer (e.g., plates or coils thermally coupled to a cooling unit) can have a temperature of about 0, 1, 2, 3, 4, 5, 6, 7, 8, 9, 10, 11, 12, 13, 14, 15, 16, 17, 18, 19 or 20° C. for making seed crystals. Typically, the seed crystals form after exposure to the surface for a few minutes, e.g., about 1, 2, 3, 4, 5, 6, 7, 8, 9, or 10 minutes (preferably 5 minutes or less). In some embodiments, after the seed crystals have formed, the temperature of the one or more cooling surfaces is adjusted to a crystallization starting temperature of about 15, 16, 17, 18, 19, 20, 21, 22, 23, 24, 25, 26, 27, 28, 29, 30, 31, 32, 33, 34 or 35° C. In some embodiments, seed crystals are not introduced, and crystallization occurs at block 214 without introducing seed crystals of I-menthol.

The crude mentha oil is crystallized at block 214 to purify the material. As an example, the crude mentha oil is added to a crystallizer and gradually cooled to obtain crystalline I-menthol. In some embodiments, the crude menthal oil is cooled from a starting temperature at which the I-menthol is a liquid to a cooled temperature in the range of about −30° C. to about 30° C. (preferably a cooled temperature in the range of about 0° C. to about 20° C.). Because the melting point of I-menthol crystals is about 42° C., crude mentha oil above that temperature can be expected to be in liquid form. However, because crude mentha oil can also be supercooled, due to slow crystal formation, especially in the absence of seed crystals, the crude mentha oil can be a liquid, for example, at 35, 36, 37, 38, 39, 40, and 41° C., or at even lower temperatures, all of which can be used as starting temperatures. The crude mentha oil may, in some embodiments, be cooled from a starting temperature in the range of about 25° C. to about 45° C. (or higher) down to a cooled temperature of about 5° C. to about 15° C. In general, I-menthol crystal formation may occur over a period of about 90-140 hours. Exemplary cooling conditions are provided in Example 1 below. Gradual cooling can result in formation of highly pure I-menthol crystals within the crystallizer.

The initial crystallization temperature (e.g., at the start time of the crystallization process, $t_c$=0) may be a temperature at which the I-menthol is a liquid. Depending on the embodiment, the initial crystallization temperature can be, for example, about 15, 16, 17, 18, 19, 20, 21, 22, 23, 24, 25, 26, 27, 28, 29, 30, 31, 32, 33, 34 or 35° C., or a higher temperature of 36, 37, 38, 39, 40, or 41° C. In some embodiments, the initial crystallization temperature can be set based upon the I-menthol concentration in the mentha oil starting material. In some embodiments, the temperature within the crystallizer can be regulated by adjusting the temperature of cooling surfaces contacting the crude mentha oil within the crystallizer. For example, the crystallizer may include one or more plates, coils, or any other surfaces, contacting the crude mentha oil within the crystallizer, where said plates, coils, or any other surfaces are thermally coupled to a cooling unit (e.g., cooled fluid is exchanged between a plate and a cooling unit). In one embodiment, the various cooling surfaces (which may also be heating surfaces) can be independently controlled by a controller in order to produce a desired temperature gradient in the crystallizer.

In general, during gradual cooling for crystallization of I-menthol, the crystallization chamber is initially cooled gradually at a rate of about 0.1-10° C. during each subsequent 24 hours or so for about the first 48 hours. The rate of cooling may be determined based on several factors. For example, the concentration of I-menthol in the crude mentha oil may be used in determining the rate of cooling. In one embodiment, the concentration of I-menthol may be determined by an I-menthol sensor that is in communication with a controller in order to automatically set and/or adjust the rate of cooling of the crystallization chamber. In other embodiments, the rate of cooling may be determined manually in response to an indicated or measured I-menthol concentration level. In one embodiment, the initial rate of cooling is more gradual (e.g., less than 1 degree per day) for an I-menthol rich crude mentha oil, while the initial rate of cooling is more rapid (e.g., about 5-10 degrees per day) for crude mentha oil with a lower concentration of I-menthol.

In one example, if the initial crystallization temperature is 25° C., at about $t_c$=24 hours, the temperature of the crystallization chamber can be adjusted to about 15° C.-24.9° C., depending on the determined initial cooling rate. For example, if the initial cooling rate is 2° C. per day, at $t_c$=24 hours the temperature would be adjusted to about 23° C. In some embodiments, the temperature is adjusted at about every 24 hours, e.g., the temperature is adjusted in a step-wise manner. In this example, using the same initial cooling rate of 2° C. per day, at about $t_c$=48 hours, the temperature of the crystallization chamber can be adjusted to about 21° C. As noted above, other cooling rates (more or less than 2° C. per day, including adjustments from 0.1° C. to 10° C. per day) and initial cooling periods (more or less than 48 hours) may be used. In some embodiments, the temperature is adjusted more gradually over a period of time.

In some embodiments, after about $t_c$=48 hours, the rate of cooling the crystallization chamber is changed from the initial cooling rate to a final cooling rate, which may be in the range of about 1-10° C. during each subsequent 24 hours or so. Thus, the final cooling rate may be about 1, 2, 3, 4, 5 or 6° C. each 24 hours or so. As noted above, the cooling rates, including the initial and final cooling rates, may be adjusted based on the concentration of I-menthol in the crude mentha oil (among other factors). Thus, for a I-menthol rich crude oil with an initial cooling rate of 0.5° C. per day, the final cooling rate may be 1-2° C. per day, while a crude mentha oil with a lower concentration of I-menthol may have an initial cooling rate of 5° C. per day and a final cooling rate of 6-10° C. per day. In other embodiments, the crude mentha oil is cooled at a single rate (e.g., the rate does not change from an initial to a final cooling rate at some point in the cooling process). In one embodiment, the rate of cooling is automatically adjusted by a controller, such as in response to sensor data indicative of crystallization progress within the crystallizer. In this embodiment, the rate of cooling (as well as the total cooling period) may be different for each crystallization process as the controller adjusts the rate in order to optimize crystallization within the crystallizer.

In some embodiments, the temperature can be adjusted about every 24 hours in a step-wise manner. In other embodiments, the temperature can be adjusted continually over a period of time, e.g., not in stepwise fashion. In general, it is preferred to reduce the temperature from a starting temperature down to a crystallization temperature in a gradual manner, over a period of at least 24, 36, or 48 hours, and then to maintain the temperature at a final crystallization temperature or continue to gradually reduce it until a desired degree of crystallization has occurred.

The total cooling time for the crystallization process is not particularly limited and will vary based on several factors, such as the cooling rate(s) and the I-menthol concentration. In some embodiments, the crystallization process can be stopped at about $t_c$=100-140 hours, at which time the dementholized oil can be removed from the crystallization chamber and the temperature of the crystallization chamber is maintained at the final crystallization temperature, which may be about 5-15° C. In some embodiments, the crystallization process is stopped when the crude mentha oil reaches a temperature in the range of about negative 20° C. to about 15° C. (e.g., about 0, 1, 2, 3, 4, 5, 6, 7, 8, 9, 10, 11, 12, 13, 14 or 15° C.). In some embodiments, the crystallization process can be stopped at, for example, about $t_c$=120 hours and the temperature within the crystallizer reaches about 10° C. In one embodiment, the total cooling time is adjusted automatically by a control in response to input from one or more sensors and or input from a human operator. Thus, the total cooling time may be dynamically adjusted for each crystallization process in order to optimize production of crystal. Generally, after the crystallization process is stopped, the temperature in the crystallizer can be maintained within a few degrees of the crystallization stopping temperature.

After crystallization, the I-menthol may optionally be further purified in a subsequent heating block 216. The heating step includes gradually elevating the temperature of the I-menthol crystals to aid in removal of impurities. Without being bound to any particular theory, it is believed that many residual impurities within the I-menthol crystal will melt at lower temperatures than the I-menthol crystals, and that impure mixtures melt at lower temperature than pure I-menthol. Consequently, gradually heating the I-menthol crystals may further increase the purity of the I-menthol. In some embodiments, at the start of purification ($t_p$=0) a surface near the bottom of the crystallization chamber is adjusted to an initial purification temperature of about 55-65° C. In other embodiments, it is not necessary to heat a surface near the bottom of the crystallization chamber at the start of purification. At $t_p$=0, the crystallization chamber is generally maintained at around the crystallization stopping temperature.

In the first few minutes of the purification process, a surface near the bottom of the crystallization chamber at an elevated temperature (if any) can be cooled quickly to about the same temperature as in the crystallization chamber. In some embodiments, to purify the I-menthol, the crystallization chamber can be gradually warmed to a temperature of about 30-40° C. In some embodiments, the crystallization chamber can be gradually warmed to a temperature at which the I-menthol remains solid. In some embodiments, the temperature is regulated to change sequentially from one temperature to another. In other embodiments, the temperature can be adjusted in a step-wise manner every 24 hours or so. In some embodiments, the temperature of the crystallizer is adjusted to reach a temperature of about 15, 16, 17, 18, 19, 20, 21, 22, 23, 24 or 25° C. at about $t_p$=24 hours. In some embodiments, the temperature of the crystallizer is adjusted to reach a temperature of about 35, 36, 37, 38, 39 or 40° C. at about $t_p$=48 hours. The temperature can be maintained at about 35-40° C. until about $t_p$=70-75 hours.

In some embodiments, the heating of I-menthol can be carried out in conjunction with applying reduced or increased pressure to facilitate removal of dementholized oil. As an example, a pressurized gas system may direct gas through the crystallizer to aid removal of melted impurities during the gradual temperature increase in the crystallizer. As another example, an aspirator can apply a vacuum to remove melted impurities from the crystallizer.

The dementholized oil that remains after the crystallization process is removed at block 218. As described above, the dementholized oil includes the remaining liquid after crystallizing the I-menthol in the crude mentha oil (e.g., after the crystallization described in block 214). In some embodiments, the dementholized oil can be removed from the crystallizer by, for example, draining by gravity, pumping and/or pressurized fluid. For example, the dementholized oil can be removed via a drain fluidly coupled to a dementholized oil tank.

In some embodiments, a fluid is passed over the I-menthol crystals to remove the dementholized oil from the crystals. In some embodiments, the fluid is a gas selected from air, an inert gas, and combinations thereof. As an example, the crystallizer may include a port near the top of the crystallizer fluidly coupled to a pressurized gas system. The pressurized gas system displaces gas, such as filtered air or nitrogen, into the crystallizer. The gas passes over the I-menthol crystals, removing oil and other impurities from the crystals, and forces dementholized oil through a drain in the crystallizer, and optionally into a dementholized oil tank. Accordingly, passing a fluid over the I-menthol crystals can both improve the purity of the crystals and expedite removing dementholized oil. In some embodiments, a reduced pressure is applied in the crystallization chamber to extract the dementholized oil. For example, an aspiration system can be fluidly coupled to the crystallizer to form a vacuum that extracts the dementholized oil. The fluid can be a liquid, a gas, or combinations thereof. In some embodiments, both increased and decreased pressure is applied. For example, an aspiration system and a pressurized air system can be fluidly coupled to the crystallizer to force fluid through the crystallizer. It will be appreciated that drawing fluid out of the bottom of the crystallizer and introducing fluid into the top of the chamber have similar results; that is, in both cases, fluid is caused to flow over the crystals and oil and other impurities are removed from the crystals and moved out of the crystallizer. Note that aspiration from the bottom and introduction of gas into the top can be combined to enhance the removal of impurities.

After completing the steps in block 210, which may or may not include optional blocks 212 and/or 216, purified I-menthol crystals are obtained at block 220. In some embodiments, the purified I-menthol crystals have at least about 98% purity by weight (preferably at least about 99% by weight). In some embodiments, the purity of the I-menthol crystals is about 99.4%, 99.5%, 99.6%, 99.7%, 99.8% or 99.9% by weight.

FIG. 2B illustrates a flow diagram of another embodiment of purifying I-menthol, where various optional pre- and post-purification steps are included. Similar blocks shown in FIGS. 2A and 2B are numbered the same. Thus, for example, both embodiments include providing crude mentha oil at block 200. As would be appreciated by a person of ordinary skill, the optional pre- and post-purification steps may be excluded or rearranged without departing from the scope of the methods disclosed herein.

An optional filtering block 205 may be performed on the crude mentha oil prior to steps performed in the crystallizer at block 210. The filtering may be used to remove impurities, such as particulates, using standard means known in the art. For example, a one micron filter can be used to filter the crude oil that is added to a crystallizer. In some embodiments, the crude oil can be passed through a filter during loading of the crystallizer. In some embodiments the crude mentha oil is directly crystallized without the optional filtration step. In some embodiments, the filtration step is automated.

After obtaining purified I-menthol at block 220, in some embodiments, the purified I-menthol can be transferred to a stock tank at optional block 225. Generally, for transferring the I-menthol, the crystallizer can be warmed to about 50-60° C. to melt the I-menthol crystals. The melted I-menthol can then be transferred to, for example, a stock tank. In some embodiments, the stock tank can be connected to the crystallizer by, for example, a conduit (e.g., lines or tubing). In some embodiments, transfer of the I-menthol can be automated.

Preferably, the stock tank can be maintained at a warm temperature. In some embodiments, the stock tank includes a heating jacket to maintain the I-menthol in a fluid state.

An optional filtering block 230 may be performed on the purified I-menthol. The filtering step may remove impurities, such as solids. In some embodiments, the crude oil can be passed through a filter during loading into a pelletizer. In some embodiments, the filtering step may be automated.

In some embodiments, the purified I-menthol can be formed into particulate for ease of handling, as shown in optional block 235. In some embodiments, solid, purified I-menthol is comminuted (e.g., grinding, milling, cutting, etc.) into particulate. In some embodiments, the particulate are pellets. The pellets may be formed, for example, using a pelletizer, from an I-menthol melt.

The pelletizer may, in some embodiments, include a cooling mixer and a pelleter. The purified I-menthol can be loaded into the cooling mixer that is maintained at a temperature of, for example, about 10-35° C. The temperature of the cooling mixer can be adjusted to about 10-35° C., preferably 15-32° C., and more preferably 17-30° C. during mixing of I-menthol. Cooling conditions are described in more detail below. In some embodiments, the I-menthol can be loaded into the cooling mixer by, for example, draining by gravity or pumping. The stock tank can be connected to the cooling mixer by, for example, a conduit. In some embodiments, transfer of the I-menthol can be automated.

In general, the initial feed temperature of the I-menthol transferred into the cooling mixer can be more than 42° C., and is preferably about 55-70° C. The material feed speed, e.g., the speed at which the I-menthol is loaded into the cooling mixer, can vary depending on the amount of I-menthol prepared, the size of the cooling mixer, etc. In some embodiments the feed speed can be about 1.0 to 3.0 kg/min. In some embodiments, the material feed speed can be, for example, about 1, 1.5 or 2 kg/min. In some embodiments, the rotation speed of the cooling mixer can be, for example, about 10, 11, 12, 13, 14, 15, 16, 17, 18, 19, 20, 21, 22, 23, 24, 25, 26, 27, 28, 29 or 30 rpm. In one embodiment, the material feed speed can be about 1.5 kg/min and the rotation speed of the cooling mixer can be about 20 rpm.

Because the melting point of I-menthol is about 42° C., under cooled mixing conditions, the I-menthol is changed to a solid state and forms a sherbet-like slurry. In some embodiments, the mixing time can be, for example, about 0.5-10 minutes, and is preferably about 1-2 minutes.

In some embodiments, a cooling mixer can include, for example, a rotor and a jacket for regulating temperature of the cooling mixer. In some embodiments, the temperature of the cooling mixer can be regulated by adjusting the temperature at, for example, the rotor inlet, the rotor outlet, the jacket inlet and/or the jacket outlet. For preparation of the I-menthol slurry, exemplary temperature conditions are set forth in Table 1 below. Columns labeled 1-6 (indicated in first row of Table 1) provide six different exemplary pelletizing conditions for preparation of I-menthol pellets having good hardness and good, non-heterogeneous shape.

TABLE 1

| Cooling Mixer Condition No. | Material Feed Temp. (° C.) | Rotor Inlet (° C.) | Rotor Outlet (° C.) | Jacket Inlet (° C.) | Jacket Outlet (° C.) |
| --- | --- | --- | --- | --- | --- |
| 1 | 58 | 11 | 12 | 31 | 32 |
| 2 | 58 | 6 | 8 | 31 | 32 |
| 3 | 58 | 10 | 11 | 31 | 32 |
| 4 | 60 | 9 | 11 | 30 | 32 |
| 5 | 60 | 9 | 11 | 30 | 32 |
| 6 | 60 | 15 | 17 | 15 | 17 |

After the I-menthol slurry is formed, the slurry can be extruded into long strands by the pelleter. In some embodiments, the I-menthol can be formed into strands by, for example, being pushed out through narrow holes of the pelleter. As a result, noodle-like strands of I-menthol can be formed. The I-menthol strands can be cut or broken into desired sizes. The diameter of the pellets can vary and will depend on the size of the pelleter holes. In some embodiments, the pellets can have a diameter of about 1, 2, 3, 4, 5, 6, 7, 8, 9, 10, 11, 12, 13, 14, 15, 16, 17, 18, 19 or 20 mm. In preferred embodiments, the pellets can have a diameter of about 3, 5 or 7 mm.

As shown in optional block 240, in some embodiments, the I-menthol can be cooled. The cooler serves to harden the I-menthol and may optionally remove low-boiling impurities. For example, pellets of I-menthol can be transferred from the pelletizer to a cooler. Any suitable means for cooling the I-menthol pellets may be used, such as a refrigerated and ventilated chamber or other cooling apparatus. In some embodiments, the I-menthol pellets can be transferred to the cooler by, for example, a conveyer belt. The conveyer belt can be enclosed to prevent foreign contaminants from contacting the I-menthol. In some embodiments, transfer of the I-menthol can be automated.

In some embodiments, the cooler can be equipped with, for example, a cool air supply system and/or a mesh tray. In some embodiments, cold air can be supplied from the bottom of the cooler. The mesh tray can be vibrated, thereby agitating and floating the I-menthol pellets to facilitate solidification.

In optional block 245, the cooled I-menthol can be transferred from the cooler to a sieve. The I-menthol can be sieved to remove small particles from the dried I-menthol. For example, I-menthol pellets may be sieved to remove particles below a predetermined size. In some embodiments, the I-menthol pellets can be transferred to the sieve by, for example, a conveyer belt. The conveyer belt can be enclosed to prevent foreign contaminants from contacting the I-menthol. In some embodiments, transfer of the I-menthol can be automated. Any suitable sieve can be used to sieve the I-menthol particulate, and various sieves are commercially available. In generally, the openings in the sieve are sized to retain particulates having the desired size and allow smaller pieces to be removed.

The I-menthol pellets can be packaged into packing containers for shipping or storage, as shown in optional block 250. In some embodiments, the I-menthol can be transferred by, for example, a conveyer belt. The conveyer belt can be enclosed to prevent foreign contaminants from contacting the I-menthol. In some embodiments, transfer of the I-menthol into packing containers can be automated.

Systems and Apparatus

Some of the present embodiments involve a system and apparatus useful for production of highly pure I-menthol. In some embodiments, the systems can automate temperature regulation during I-menthol production. To accomplish temperature control for production of highly pure I-menthol crystals, the system can include a crystallizer that receives crude mentha oil. The crystallizer includes heating and cooling structures, such as, for example without limitation, plates, coils, plate-coils, or any other suitable device, which provide surfaces for I-menthol crystal nucleation and growth. In some embodiments, the system forms a closed system that prevents contact between the content of the closed system and outside contaminants.

With reference now to FIG. 3, an exemplary system for purifying I-menthol is illustrated. In the embodiment shown in FIG. 3, the crystallizer 300 comprises heating/cooling plates 305, but in other embodiments the crystallizer 300 may comprise alternative and/or additional heating and/or cooling devices. The plates 305 can be any size and shape for providing a suitable surface for growth of I-menthol crystals and are located in the crystallizer 300. Crude mentha oil can be added directly into the crystallizer (the crystallization chamber). When crude mentha oil is added to the crystallizer, it comes into contact with plates 305. In some embodiments, the structure of the heating/cooling plates 305 can be, for example without limitation, flat plates, coils, radiator-like coils, etc. In some embodiments, plates 305 are plate-coils set closely together (e.g., about 2.5 to about 10 cm between each plate). Generally, plates 305 can precisely control the temperature inside the crystallizer 300, such as in response to control signals from a controller.

In the embodiment of FIG. 3, conduits 310 connect the plates 310 to a heating/cooling unit (e.g., as illustrated by in FIG. 4A by cooling unit 410 and heating unit 415). As an example, fluid enters plates 305 through conduits 310, and then the fluid circulates back to a heating/cooling unit. The temperature of plates 305 is controlled by heating or cooling the circulating fluid. In some embodiments, plates 305 are thermally coupled to a heating/cooling unit. In some embodiments, the temperature of each of plates 305 can be independently controlled. For example, each plate may receive separately circulated fluids that can have different temperatures. In some embodiments, the temperature of the bottom and the side walls in the chamber can be independently controlled by another heating or cooling unit.

The temperature of crystallizer 300 can be controlled for production of highly pure I-menthol crystals, as described above with respect to methods of purifying I-menthol. The temperature of plates 305 in crystallizer 300 may also be adjusted to a desired temperature. In some embodiments, the temperature of the one or more plates of the crystallizer can each be adjusted to different temperatures (e.g., in response to control signals from a controller and/or from a human operator). In some embodiments, all the plates of the crystallizer can be the same temperature In some embodiments, one or more plates 305 in the crystallizer 300 can include one or more temperatures sensors 307.

In some embodiments, plates 305 of crystallizer 300 can include a cooling/heating medium for regulating temperature. As used herein "cooling/heating medium" refers to a medium that can be used to regulate temperature, including cooling and heating. For example, media such as, for example without limitation, solvents or refrigerants, cryogenic substances or other suitable substances can be added to the cooling/heating device for regulating temperature.

Various ports may be included in the crystallizer to exchange material in the crystallizer. The crystallizer may optionally include drain 312 configured for removing liquid from the crystallizer. In some embodiments, drain 312 is fluidly coupled to an aspiration unit (e.g., as illustrated in FIG. 4B by aspiration system 425) to withdraw liquid from the crystallizer. In some embodiments, drain 312 may be used for removing liquid from the crystallizer. The crystallizer may also include port 315 for directing a fluid into the crystallizer. For example, a pressurized gas system (e.g., as illustrated in FIG. 4A by pressurized air system 420) may be fluidly coupled to port 315, and pressurized air can be forced into the crystallizer through this port 315. As discussed above, the pressurized air can force dementholized oil off of the crystals and out of the crystallizer through drain 312.

FIG. 4A illustrates another embodiment of the system for purifying I-menthol. In some embodiments, the system for I-menthol production can be controlled by user defined processing parameters via automated process control system 400 (hereinafter "controller"). Depending on the embodiment, controller 400 may comprise one or more computing systems, such as a desktop, notebook, or portable computing device; or integrated circuits, such as field programmable gate arrays (FPGAs), application specific integrated circuits (ASICs), microcontrollers, or proprietary logic circuits. In one embodiment, controller 400 comprises (and/or is in communication with) one or more input devices, such as a touchscreen, mouse, or keyboard, and one or more output devices, such as a monitor or display of a mobile device, so that the controller may display information regarding the status of the I-menthol production system to an operator of the system and receive control instructions from the operator. With the use of controller 400, the system can be partially or fully automated for I-menthol production, including automation of temperature control, air pressure control, aspiration, draining, mixing, transport of I-menthol, pelleting, drying, sieving and packing with user defined processing parameters. In some embodiments, the system can be programmable for desired time periods and temperature settings for optimal I-menthol production. The system can also be programmable for pressure settings, moisture control settings, vapor evacuation, sample loading, etc. In some embodiments, controller 400 can include a program storage function. In other embodiments, the system can be controlled manually by user input at each stage in production. In some embodiments, the system can include safeguards for accommodating problems which may arise during processing such as, for example, exceeding desired temperature ranges, pressure or leakage problems, power failures, etc.

In some embodiments, controller 400 is in communication with crystallizer 405 (e.g., as illustrated in FIG. 3 by crystallizer 300) and can be used to regulate the temperature in crystallizer 405. For example, controller 400 can be programmed to increase and decrease the temperature of the various parts of the crystallizer (e.g., heating/cooling plates) as desired. In some embodiments, temperature sensors (e.g., as illustrated in FIG. 3 by temperature sensors 307) for heating/cooling surfaces of the crystallizer can provide temperature data to the controller. In some embodiments, the data from the temperature sensors can be used to adjust temperature of the various parts of the crystallizer.

Controller 400 may be in communication with cooling unit 410 and heating unit 415. As discussed above, cooling unit 410 and heating unit 415 may be thermally coupled to the crystallizer. For example, fluid may be exchanged between heating/cooing units and plates within the crystallizer. Thus, in some embodiments, the control may regulate the temperature within the crystallizer by controlling operation of cooling unit 410 and heating unit 415, which are thermally coupled to the crystallizer. Crystallizer 405, cooling unit 410 and heating unit 415 may, in some embodiments, form a single unit in communication with controller 400.

In some embodiments, controller 400 comprises a processor programmed (e.g., executing software code stored on a computer readable medium, such as a memory (RAM, ROM, Flash memory, etc.), a hard drive, and/or optical storage medium of the controller) to automate any of the methods for purifying I-menthol disclosed above. For example, the processor may be programmed to crystallize the crude mentha oil by automatically reducing and maintaining temperatures as described for crystallization block 214 in FIG. 2A. As another example, the processor may be programmed to perform any of the tasks performed within the crystallizer (e.g., any of the steps within block 210 in FIG. 2A). The processor may be programmed, in some embodiments, to gradually reduce the temperature of crude mentha oil in the crystallizer from a temperature at which the crude mentha oil is a liquid to a temperature below 30° C. in a gradual manner over a period of at least 8 hours to cause I-menthol crystals to form in the crystallizer. In some embodiments, the processor may be programmed to heat and/or melt the purified I-menthol crystal after dementholized oil has been removed from the crystallizer. In some embodiments, the processor is programmed to heat the I-menthol crystals gradually to a temperature below 40° C. to remove impurities from the crystals.

The controller 400, in some embodiments, selects conditions for crystallizing the I-menthol (e.g., temperature, cooling rate, etc.), at least in part, based upon a received identifier that corresponds to the I-menthol concentration in the crude mentha oil. For example, controller 400 may be in communication with optional sensor 417 that determines the I-menthol concentration. After receiving the I-menthol concentration, controller 400 may select appropriate crystallizing conditions. As another example, a user may enter the concentration at a user interface in communication with controller 400.

In some embodiments, the system may include an optional crystal detector 419 that is configured to detect the presence of I-menthol crystals within the crystallizer. Controller 400 can be in communication with the crystal detector to identify when crystals have formed and the degree of crystallization in the crystallizer. In some embodiments, the controller includes a processor configured to lower the temperature in the crystallizer to suitable conditions for seed crystal formation (e.g., conditions for introducing seed crystals at block 212 in FIG. 2A). Once seed crystals are detected by the seed crystal detector, controller 400 may adjust the temperature to a temperature suitable for crystallization (e.g., conditions suitable for crystallization block 214 in FIG. 2A). Once the system detects the presence of sufficient crystals to indicate that crystallization has completed to the desired degree, the dementholized oil can be removed from the crystallizer, under either manual or automatic control.

In some embodiments, the seed crystal detector comprises a light source and a light detector configured to detect changes in the optical properties of material in the crystallizer. Thus, for example, crystallized I-menthol may exhibit higher light scattering compared to liquid crude mentha oil, which may be detected. In some embodiments, the optional crystal detector comprises a detector in the cooling circuit configured to measure heat removal by a cooling surface, and a thermocouple configured to measure the temperature near the cooling surface. As an example, the relationship between the heat removal and temperature may be used to detect crystallization. Note that crystallization releases heat, so that while crystallization is occurring, heat energy is removed from the crude mentha oil without the same decrease in temperature in the crystallizer as would occur if no crystallization were occurring.

The system can include a pressurized air or gas system 420 to aid in removal of dementholized oil from crystals. For example, during purification of I-menthol crystals, pressurized air system 420 can provide pressurized gas to the chamber of the crystallizer to facilitate removal of dementholized oil from the surface of I-menthol crystals. The controller 400 may be in communication with pressurized air system 420 and may control applying pressurized air at an appropriate time in the process (e.g., at extraction block 218 in FIG. 2A).

FIG. 4B illustrates another embodiment of a system disclosed herein. Similar components to those in FIG. 4A are numbered the same (e.g., FIGS. 4A and 4B both have crystallizer 405). The system includes an aspiration system 425 fluidly coupled to crystallizer 400. As described above, the aspiration system may be used to reduce the pressure in the crystallizer and extract dementholized oil. In some embodiments, controller 400 is in communication with aspiration system 425 to apply reduced pressure at an appropriate time (e.g., at extraction block 218 in FIG. 2A). In some embodiments, the system includes both pressurized air system 420 and aspiration system 425.

As used herein, a "stripping system" refers to any components configured to aid removal of dementholized oil by adjusting the pressure. Thus, a stripping system is a broad term that would include pressurized air system 420, aspiration system 425, and combinations thereof.

FIG. 4C illustrates another embodiment of a purification system having various optional components. Similar components to those in FIGS. 4A and 4B are numbered the same (e.g., FIGS. 4A, 4B and 4C all have crystallizer 405). As would be appreciated by a person of ordinary skill, various optional components may be excluded or rearranged without departing from the scope of the present invention.

In some embodiments, the system can include dementholized oil tank 430 for storage of dementholized oil tank that has been removed from the crystallizer. For example, after crystallization, the dementholized oil tank can be pumped or drained from the crystallizer into dementholized oil tank 430 (e.g., at extraction block 218 illustrated in FIG. 2A). Transfer of the dementholized oil from the crystallizer to the dementholized oil tank 430 can be automated.

In some embodiments, the system can include a stock tank 435 for storage of I-menthol that has been removed from the crystallizer. For example, after purification (e.g., at block 220 in FIGS. 2A and 2B), the I-menthol crystals in crystallizer 400 can be melted and pumped or drained from the crystallizer chamber into stock tank 435 (e.g., as illustrated in block 225 in FIG. 2B). Preferably, stock tank 435 is connected to the crystallizer via a conduit. In some embodiments, stock tank include a heating unit to maintain the I-menthol at a temperature at which the I-menthol is a liquid. The transfer of the I-menthol from crystallizer 400 to the stock tank 435 can be automated.

In some embodiments, the system can include pelletizer 440 for shaping the I-menthol into pellets for ease of handling (e.g., as illustrated in forming particulate block 235 in FIG. 2B). As described above, pelletizer 440 may include a cooling mixer for mixing the menthol prior to pellet formation. Depending on the embodiment, the cooling mixer may comprise a proprietary cooling mixer, such as a mixer that is integrally coupled with a pelleter, and/or a commercially available cooling mixer (e.g., the Krimoto, Ltd. SC Processor model number SCP-100, and others). In some embodiments, pelletizer 440 can be connected to stock tank 435 or to the crystallizer via a conduit for hands-free transfer of liquid I-menthol to the cooling mixer. In some embodiments, controller 400 is in communication with pelletizer 440. The transfer of the I-menthol from the stock tank or the crystallizer to the cooling mixer can be automated.

The temperature of the cooling mixer can be regulated to ensure that the I-menthol is at the correct temperature for forming pellets having the desired hardness, shape, air content, etc. In some embodiments, purified I-menthol can be loaded into the cooling mixer. The purified I-menthol is typically loaded into the cooling mixer in liquid form. In general, the initial feed temperature of the I-menthol is about 45-65° C. The cooling mixer can be equipped with, for example, a cooling jacket that can regulate the temperature of the cooling mixer. Generally, the temperature of the cooling mixer can be maintained between about 5 to about 40° C. during, for example, mixing of the I-menthol for pellet formation.

Pelletizer 440 may further include a pelleter. In some embodiments, the pelleter can include a plate having holes through which solidified, sherbet-consistency I-menthol can be extruded through and shaped into a noodle-like form. In some embodiments, the I-menthol can be pushed by, for example, means of a rotating screw inside the pelleter. The menthol transfer speed can be changed by the rotation speed. I-Menthol is extruded through the holes of the plate, forming long, noodle-like strands. The size of the holes of the plate can vary depending on the desired pellet size, and is not meant to be limited to any particular size. In some embodiments, the holes can have a diameter of, for example, about 1, 2, 3, 4, 5, 6, 7, 8, 9, 10, 11, 12, 13, 14, 15, 16, 17, 18, 19 or 20 mm. Pelleters are commercially available and include, for example without limitation, the Dulton Corp. Pelleter Double model number EKDFJ-100. The pelletizer may also include a cutter configured to cut the strands into desired lengths. As an example, the cutter may be a rotating blade that cuts the extruded strands at predetermined time intervals.

In some embodiments, the I-menthol production system includes cooler 445 for cooling the I-menthol pellets (e.g., as illustrated in cooling block 240 in FIG. 2B). In some embodiments, the pellets can be transferred from pelletizer 440 to the cooler 445 by, for example, an enclosed conveyer belt. Transfer of the I-menthol from the pelletizer 440 to the cooler 445 can be automated. Generally, cooler 445 includes cooled air flow to aid hardening of the I-menthol. In some embodiments, the cooler 445 can include, for example, vibrating mesh platforms for agitation of the pellets and facilitating solidification of the I-menthol. Preferably, the cooler is enclosed to prevent contaminants from contacting the I-menthol. In addition, filters can be used in conjunction with the dryer to ensure that the air flowing over the I-menthol pellets is clean and pure. In some embodiments, drying of the I-menthol pellets can be automated, such as by control signals from controller 400.

In some embodiments, the I-menthol production system includes sieve 450. Sieve 450 can be used to remove small particles from the dried I-menthol pellets (e.g., as illustrated by sieving block 245 in FIG. 2B). In some embodiments, the pellets can be transferred from the dryer to the sieve by, for example, an enclosed conveyer belt. Preferably, sieve 450 is enclosed to prevent contaminants from contacting the I-menthol. In some embodiments, sieving of the I-menthol pellets can be automated, such as by control signals from controller 450.

In some embodiments, the I-menthol production system includes packing containers 455 for packaging the I-menthol. For example, a conveyer belt or other conveyer (e.g., pneumatic conveyer, screw conveyer) from the sieve 450 can be used to transfer I-menthol pellets from sieve 450 to packing containers 455. In some embodiments, the conveyer belt can be enclosed to prevent contaminants from contacting the I-menthol. In some embodiments, packaging of the I-menthol can be automated. In some embodiments, the packaging containers are fluidly connected to stock tank 435. Liquid I-menthol may be directly loaded into packing containers 455, and the I-menthol cooled to a solid within the containers.

In some embodiments, controller 400 executes computer software that controls the various parameters for I-menthol production. In some embodiments, the software accepts user input for each factor, for example, temperature, air pressure, aspiration, drainage, transport, mixing, pelleting, drying, sieving, and packing. In this manner, I-menthol production can be automated. In some embodiments, the software performs any of the methods described herein.

EXAMPLES

Aspects of the present teachings can be further understood in light of the following examples, which should not be construed as limiting the scope of the present teachings in any way.

Example 1

This example illustrates possible methods for production of I-menthol having a purity of 99.6% or greater.

Crude mentha oil (I-menthol purity of about 80%) was transferred from drums to a crystallizer through a one micron filter. The crystallizer included cooling plates on which I-menthol crystals could nucleate and grow. I-Menthol crystals were formed by slow, step-wise cooling of the crystallization chamber from about 25° C. down to about 10° C. over about a 120 hour period, then maintaining the chamber temperature at about 10° C. for about 24 hours. Table 2 shows the temperature of the sides, bottom and cooling plate of the crystallization chamber at various time points during the crystallization process. At then end of about 120 hours, highly pure I-menthol crystals were formed on the plates of the crystallizer.

TABLE 2

| | Temperature (degree Centigrade) | | |
|---|---|---|---|
| Time | Sides of Chamber | Bottom of Chamber | Cooling Plates |
| 0 | 30 | 30 | 10 |
| 5 min. | 25 | 25 | 25 |
| 24 hr. | 23 | 23 | 23 |
| 48 hr. | 21 | 21 | 21 |
| 72 hr. | 16 | 16 | 16 |
| 96 hr. | 10 | 10 | 10 |
| 120 hr. | Stop | | |

After crystallization, the dementholized oil was drained by gravity from the bottom of the crystallizer into a separate tank.

After removal of the dementholized oil, I-menthol crystals were purified while still in the crystallization chamber. The I-menthol purification process was carried out using aspiration and gradual heating of the I-menthol crystals. The bottom valve of the crystallizer was opened, and aspiration was started. The temperature of the crystallization chamber was gradually increased to about 35° C. over about a 48 hour time period, and the I-menthol was maintained at about 35° C. for about 2 to 4 hours. Temperature conditions for the sides, bottom and cooling plates of the crystallizer are provided below in Table 3.

TABLE 3

| Time | Temperature (degree Centigrade) | | |
|---|---|---|---|
| | Sides of Chamber | Bottom of Chamber | Cooling Plates |
| 0 | 10 | 60 | 10 |
| 5 min. | 10 | 10 | 10 |
| 24 hr. | 20 | 20 | 20 |
| 48 hr. | 35 | 35 | 35 |
| 72 hr. | Stop | | |

After purification, the I-menthol was removed from the crystallizer by heating the crystallization chamber to about 60° C. to melt the I-menthol crystals. The sides, bottom and cooling plates of the crystallization chamber were heated to about 60° C. After about 5 hours, the bottom valve of the crystallizer was connected to a stock tank, and the melted I-menthol was transferred to the stock tank. The purified I-menthol had a purity of about 99.6%.

Example 2

This example illustrates possible methods for I-menthol pelletization and cooling.

The highly pure I-menthol produced by the method described in Example 1 was formed into pellets for ease of handling. A pelletizer including a cooling mixer and pelleter was used. The I-menthol was transferred from the stock tank to the cooling mixer of a pelletizer at a rate of about 200 kg/hr. In the cooling mixer, the I-menthol was mixed at about 15° C. for minutes to form a sherbet-like slurry.

Pellets were formed by extruding the I-menthol slurry through the pelleter and cutting the resulting I-menthol strands into desired lengths. The pelleter outlet was maintained at about 5° C. The pellets were transferred to a dryer and dried using an air flow speed of about 0.9 cubic meters per minute at about 25° C.

Example 3

This example illustrates a preliminary study to determine pelletization conditions using a cooling mixer and pelleter.

The highly pure I-menthol produced by the method described in Example 1 was formed into pellets using a variety of different conditions to determine the conditions suitable for preparing I-menthol tablets having good hardness and good shape. Conditions used and results from eighteen different pelletization experiments are summarized in Tables 4 and 5 below. The I-menthol was transferred from the stock tank to the cooling mixer of a pelletizer at a rate of about 1.5 kg/hr. In the cooling mixer, the I-menthol was mixed under the conditions shown to form a slurry. The I-menthol slurry was formed into long strands and cut into desired lengths.

TABLE 4

| | Exp. No. | | | | | | | | |
|---|---|---|---|---|---|---|---|---|---|
| | 01 | 02 | 03 | 04 | 05 | 06 | 07 | 08 | 09 |
| cooling mixer: | | | | | | | | | |
| Material feed temp (° C.) | 58 | 58 | 58 | 58 | 60 | 60 | 60 | 60 | 65 |
| Material feed speed (kg/min) | 1.5 | 1.5 | 1.5 | 1.5 | 1.5 | 1.5 | 1.5 | 1.5 | 1.5 |
| Rotor inlet temp (° C.) | 11 | 6 | 4 | 10 | 4 | 8 | 9 | 11 | 8 |
| Rotor outlet temp (° C.) | 12 | 8 | 7 | 11 | 10 | 11 | 13 | 13 | 9 |
| Jacket inlet temp (° C.) | 31 | 31 | 4 | 31 | 30 | 30 | 30 | 30 | 30 |
| Jacket outlet temp (° C.) | 32 | 32 | 7 | 32 | 32 | 32 | 32 | 32 | 32 |
| Rotation speed (rpm) | 20 | 20 | 20 | 20 | 20 | 20 | 20 | 20 | 20 |
| pelleter: | | | | | | | | | |
| Rotation speed (rpm) | 60 | 60 | 60 | 60 | 60 | 60 | 60 | 60 | 60 |
| Hole diameter (mm) | 5 | 5 | 5 | 5 | 5 | 5 | 5 | 5 | 5 |
| Results: | | | | | | | | | |
| Pellet hardness (G = good, H = too hard, S = too soft) | G | G | G | G | H | H | G | S | S |
| Pellet shape (G = good, H = heterogeneous) | G | G | H | G | H | H | G | G | G |

TABLE 5

| | Exp. No. | | | | | | | | |
|---|---|---|---|---|---|---|---|---|---|
| | 10 | 11 | 12 | 13 | 14 | 15 | 16 | 17 | 18 |
| cooling mixer: | | | | | | | | | |
| Material feed temp (° C.) | 58 | 58 | 58 | 58 | 60 | 60 | 60 | 60 | 65 |
| Material feed speed (kg/min) | 1.5 | 1.5 | 1.5 | 1.5 | 1.5 | 1.5 | 1.5 | 1.5 | 1.5 |
| Rotor inlet temp (° C.) | 9 | 9 | 10 | 11 | 15 | 17 | 15 | 15 | 15 |
| Rotor outlet temp (° C.) | 11 | 11 | 12 | 13 | 17 | 19 | 17 | 17 | 17 |
| Jacket inlet temp (° C.) | 30 | 30 | 30 | 11 | 15 | 17 | 15 | 15 | 15 |
| Jacket outlet temp (° C.) | 32 | 32 | 32 | 13 | 17 | 19 | 17 | 17 | 17 |
| Rotation speed (rpm) | 20 | 20 | 20 | 20 | 20 | 20 | 20 | 20 | 20 |
| pelleter: | | | | | | | | | |
| Rotation speed (rpm) | 60 | 60 | 60 | 60 | 60 | 60 | 60 | 60 | 60 |
| Hole diameter (mm) | 5 | 5 | 5 | 5 | 5 | 5 | 3 | 5 | 7 |
| Results: | | | | | | | | | |
| Pellet hardness (G = good, H = too hard, S = too soft) | G | H | H | H | G | S | G | G | G |
| Pellet shape (G = good, H = heterogeneous) | G | H | H | H | G | G | G | G | G |

Results from the eighteen experiments shown in Tables 4 and 5 demonstrate that depending on the conditions used during pelletization, the pellet hardness and shape can vary. The pelletization conditions used in experiments 01, 02, 04, 07, 10, 14, 16, 17 and 18 resulted in pellets having both good hardness and good, non-heterogeneous shape.

It is to be understood that both the foregoing general description and the detailed description are exemplary and explanatory only and are not restrictive of the invention, as claimed. In this application, the use of the singular includes the plural unless specifically stated otherwise. In this application, the word "a" or "an" means "at least one" unless specifically stated otherwise. In this application, the use of "or" means "and/or" unless stated otherwise. Furthermore, the use of the term "including," as well as other forms, such as "includes" and "included," is not limiting. Also, terms such as "element" or "component" encompass both elements or components comprising one unit and elements or components that comprise more than one unit unless specifically stated otherwise.

The section headings used herein are for organizational purposes only and are not to be construed as limiting the described subject matter in any way.

It will be appreciated that there can be an implied "about" prior to the temperatures, concentrations, times, etc. discussed in the present teachings, such that slight and insubstantial deviations are within the scope of the present teachings herein. Also, the use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the invention.

INCORPORATION BY REFERENCE

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application; including but not limited to defined terms, term usage, described techniques, or the like, this application controls.

EQUIVALENTS

The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. A method for purifying 1-menthol, comprising:
providing crude mentha oil in a crystallizer, wherein the crude mentha oil is from a mint plant and comprises 1-menthol in the range of about 50% to about 95% by weight, and wherein the crude mentha oil is free of organic solvents;
crystallizing 1-menthol from the crude mentha oil by gradually reducing temperature in the crystallizer from a starting temperature at which the 1-menthol is a liquid to a cooled temperature in the range of −30° C. to 25° C. at a cooling rate in the range of 0.1° C./day to 10° C./day to form 1-menthol crystals;
passing a gas over the 1-menthol crystals to remove residual oil and impurities while gradually elevating the temperature in the crystallizer to a temperature in the range of 30° C. to 40° C., wherein purified 1-menthol crystals of at least 98% purity by weight are obtained;

melting the purified 1-menthol crystals to remove 1-menthol from the crystallizer as a melt; and cooling the melt into a dried, solid 1-menthol product, wherein the method is performed in a closed system without human contact with the crude mentha oil or the 1-menthol.

2. The method of claim 1, wherein the 1-menthol product has a purity of at least 99% by weight.

3. The method of claim 1, wherein the temperature in the crystallizer is gradually reduced to between about 0° C. to about 20° C.

4. The method of claim 1, further comprising comminuting the solid 1-menthol product into particulate.

5. The method of claim 4, wherein the particulate are pellets.

6. The method of claim 1, further comprising introducing seed crystals of 1-menthol into the crystallizer to aid crystallizing 1-menthol.

7. The method of claim 1, further comprising applying reduced or increased pressure to aid removing residual oils and impurities while gradually elevating the temperature in the crystallizer.

8. The method of claim 1, wherein the purified 1-menthol crystals are obtained by crystallizing the crude mentha oil only once.

\* \* \* \* \*